(12) United States Patent
McDonough et al.

(10) Patent No.: US 9,028,873 B2
(45) Date of Patent: *May 12, 2015

(54) NANOPARTICLES FOR DRUG DELIVERY TO THE CENTRAL NERVOUS SYSTEM

(75) Inventors: Joseph A. McDonough, Helotes, TX (US); Hong Dixon, Helotes, TX (US); Larry A. Cabell, San Antonio, TX (US)

(73) Assignee: Southwest Research Institute, San Antonio, TX (US)

(*) Notice: Subject to any disclaimer, the term of this patent is extended or adjusted under 35 U.S.C. 154(b) by 25 days.

This patent is subject to a terminal disclaimer.

(21) Appl. No.: 12/702,095

(22) Filed: Feb. 8, 2010

(65) Prior Publication Data

US 2011/0195125 A1 Aug. 11, 2011

(51) Int. Cl.
| | |
|---|---|
| *A61K 9/14* | (2006.01) |
| *A61K 31/444* | (2006.01) |
| *A61P 25/00* | (2006.01) |
| *B32B 5/00* | (2006.01) |
| *A61K 9/50* | (2006.01) |
| *A61K 9/51* | (2006.01) |

(52) U.S. Cl.
CPC ......... *A61K 31/444* (2013.01); *Y10T 428/2982* (2015.01); *A61K 9/5021* (2013.01); *A61K 9/5115* (2013.01); *Y10S 977/773* (2013.01); *Y10S 977/906* (2013.01)

(58) Field of Classification Search
None
See application file for complete search history.

(56) References Cited

U.S. PATENT DOCUMENTS

| | | | |
|---|---|---|---|
| 2,305,947 A | 8/1942 | Armstrong et al. | |
| 2,305,917 A | 12/1942 | Armstrong | |
| 2,816,113 A | 12/1957 | Wilson | |
| 3,135,761 A | 6/1964 | Hackley et al. | |
| 3,137,702 A | 6/1964 | Luttringhaus | |
| 3,629,425 A | 12/1971 | Hussain | |
| 3,929,813 A | 12/1975 | Higuchi et al. | |
| 4,128,651 A | 12/1978 | Hagedorn | |
| 4,305,947 A | 12/1981 | Bartner | |
| 4,540,602 A | 9/1985 | Motoyama et al. | |
| 4,705,777 A | 11/1987 | Lehrer et al. | |
| 4,880,610 A | 11/1989 | Constantz | |
| 5,130,438 A | 7/1992 | Hsiao et al. | |
| 5,145,684 A | 9/1992 | Liversidge et al. | |
| 5,298,504 A | 3/1994 | Sommer et al. | |
| 5,589,167 A | 12/1996 | Cleland | |
| 5,662,883 A | 9/1997 | Bagchi et al. | |
| 5,716,642 A | 2/1998 | Bagchi et al. | |
| 5,770,181 A | 6/1998 | Kirkland | |
| 5,902,816 A * | 5/1999 | Viner | 514/334 |
| 5,929,093 A * | 7/1999 | Pang et al. | 514/332 |
| 6,007,845 A | 12/1999 | Domb et al. | |
| 6,117,454 A | 9/2000 | Kreuter et al. | |
| 6,355,271 B1 | 3/2002 | Bell et al. | |
| 6,395,029 B1 | 5/2002 | Levy et al. | |
| 6,656,505 B2 | 12/2003 | Kundu et al. | |
| 6,815,543 B1 | 11/2004 | Bernardelli | |
| 6,861,068 B2 | 3/2005 | Ng et al. | |
| 6,881,745 B2 | 4/2005 | Hayes et al. | |
| 7,037,528 B2 | 5/2006 | Kipp et al. | |
| 7,081,161 B2 | 7/2006 | Genge et al. | |
| 7,282,194 B2 | 10/2007 | Sung et al. | |
| 7,300,670 B2 | 11/2007 | Venus et al. | |
| 7,387,792 B2 | 6/2008 | Hirsh et al. | |
| 7,390,384 B2 | 6/2008 | Fang et al. | |
| 8,309,134 B2 | 11/2012 | McDonough et al. | |
| 8,404,850 B2 | 3/2013 | Cabell et al. | |
| 8,722,706 B2 | 5/2014 | Dixon et al. | |
| 2003/0073619 A1 | 4/2003 | Mahato et al. | |
| 2004/0022820 A1 | 2/2004 | Anderson | |
| 2004/0256749 A1 | 12/2004 | Chaubal et al. | |
| 2004/0266890 A1 | 12/2004 | Kipp et al. | |
| 2005/0106257 A1 | 5/2005 | Albayrak | |
| 2005/0113489 A1 | 5/2005 | Baran, Jr. et al. | |
| 2005/0118108 A1 | 6/2005 | Cowan et al. | |
| 2005/0202093 A1 * | 9/2005 | Kohane et al. | 424/489 |
| 2005/0220888 A1 | 10/2005 | Putcha et al. | |
| 2006/0063662 A1 | 3/2006 | Hata et al. | |
| 2006/0183777 A1 | 8/2006 | Huang et al. | |
| 2006/0216353 A1 | 9/2006 | Liversidge et al. | |
| 2007/0093518 A1 | 4/2007 | Wetherell et al. | |
| 2007/0134339 A1 | 6/2007 | Jenkins et al. | |
| 2007/0190160 A1 | 8/2007 | Turos et al. | |
| 2008/0107736 A1 | 5/2008 | McDonough et al. | |

(Continued)

FOREIGN PATENT DOCUMENTS

| | | |
|---|---|---|
| EP | 1319400 | 6/2003 |
| WO | 9814587 | 4/1998 |

(Continued)

OTHER PUBLICATIONS

Hobbiger, Biochemical Journal, 75, 1960.*
Kuca, Journal of Applied Toxicology, 25, 2005.*
Gao, International Journal of Pharmaceutics, 310, 2006.*
Macauley, Journal of Phamraceutical and Biomedical Analysis, 49, 2009.*
Bagryanskaya, Russion Chemical Bulletin, International Edition, 50, 11, 2001.*
Kreuter, Journal of Drug Targeting, 10, 4, 2002.*
Wu, Pharmaceutical Research, 16, 3, 1999.*
Liu, Biomaterial, 29, 2008.*
Radic, et al., "Evaluation of HI-6 oxime: potential use in protection of human acetylcholinesterase inhibited by antineoplastic drug irinotecan and its cyto/genotoxicity in vitro," Acta Biochimica Polonica vol. 54 No. Mar. 2007, 583-593, Aug. 23, 2007.

(Continued)

*Primary Examiner* — Susan Tran
*Assistant Examiner* — William Craigo
(74) *Attorney, Agent, or Firm* — Grossman, Tucker et al

(57) ABSTRACT

The present disclosure relates to compositions and methods for producing nanoparticles to provide relatively more rapid delivery of such particles across the blood-brain barrier. The nanoparticles may be formed from bis-quaternary pyridinium-aldoxime salts that may also be of a specific polymorphic structure and which may be formed in either hydrophobic or hydrophilic type liquid media. In addition, the nanoparticle for transport across the blood-brain barrier may comprise a polymeric resin encapsulating a bis-quaternary pyridinium-2-aldoxime salt.

12 Claims, 10 Drawing Sheets

(56) References Cited

U.S. PATENT DOCUMENTS

| | | | |
|---|---|---|---|
| 2008/0145439 | A1 | 6/2008 | Lobl et al. |
| 2008/0241256 | A1 | 10/2008 | Kuhn |
| 2009/0263491 | A1 | 10/2009 | Kreuter et al. |
| 2009/0281144 | A1 | 11/2009 | Cabell et al. |
| 2009/0304720 | A1 | 12/2009 | Kreuter et al. |
| 2010/0040692 | A1 | 2/2010 | Dixon et al. |
| 2010/0086601 | A1 | 4/2010 | McDonough et al. |

FOREIGN PATENT DOCUMENTS

| | | |
|---|---|---|
| WO | 9841188 | 9/1998 |
| WO | 0163362 | 8/2001 |
| WO | 0232402 | 4/2002 |
| WO | 2004073033 A2 | 8/2004 |
| WO | 2005123581 | 12/2005 |
| WO | 2007/001355 A2 | 1/2007 |
| WO | 2007/084460 A2 | 7/2007 |
| WO | 2009114298 | 9/2009 |
| WO | 2010019398 A1 | 2/2010 |
| WO | 2010040057 A1 | 4/2010 |

OTHER PUBLICATIONS

Stojiljkovic, et al., "Pryidinum Oximes: Rationale for their Selection as casual Antidotes against Organophosphate Poisonings and current solutions for auto-injectors," Arh Hig Toksikol 2006, 57:435-443.

Praetorius, et al., "Engineered Nanoparticles in Cancer Therapy," Recent Patents on Drug Delivery & Formation 2007,vol. 1 No. 1, pp. 37-51.

Biosante Pharmaceuticals, "Hormone Therapy-A Multi-Billion Dollar Market," Investor Fact Sheet Sep. 2007; www.biosantepharma.com; (2 pages).

T.Welzel, et al., "Transfection of Cells With Custom-made Calcium Phosphate Nanoparticles Coated With DNA"; The Royal Society of Chemistry 2004; J. Mater. Chem. 2004, 14, pp. 2213-2217.

S. Bisht, et al., "pDNA Loaded Calcium Phosphate Nanoparticles: Highly Efficient Non-Viral Vector for Gene Delivery"; International Journal of Pharmaceutics 288 (2005), pp. 157-168.

T.Liu, et al., "Calcium Phosphate Nanoparticles as a Novel Nonviral Vector for Efficient Transfection of DNA in Cancer Gene Therapy"; Cancer Biotherapy & Radiopharmaceuticls, vol. 20, No. 2, 2005, pp. 141-150.

A. Brioschi, et al, "Solid Lipid Nanoparticles: Could They Help . . ."; Neurological Research 2007, vol. 29, Apr. 2007; pp. 324-330.

M. Nahar, et al, "Functional Polymeric Nanoparticles: An Efficient . . . "; Critical Reviews ™ In Therapeutic Drug Carrier Systems, 23(4):259-318 (2006); Begell House Inc., http://begellhouse.com; downloaded Sep. 18, 2009 from IP 129.162.1.41 by Celia Frausto.

Gelperina, et al., "Drug delivery to the brain using surfactant-coated poly(lactide-co-glycolide) nanoparticles: Influence of the formulation parameters," European Journal of Pharmaceutics and Biopharmaceutics (2009) doi:10.1016/j.ejpb.2009.09.003.

Kurakhmaeva, et al, "Brain targeting of nerve growth factor using poly(butyl cyanoacrylate) nanoparticles," Journal of Drug Targeting, 2009; 17(8): 564-574.

Hekmatara, et al., "Efficient systemic therapy of rat glioblastoma by nanoparticle-bound doxorubicin is due to antiangiogenic effects," Clinical Neuropathology, vol. 28—No. Mar. 2009 (153-164).

Zensi, et al., "Albumin nanoparticles targeted with Apo E enter the CNS by transcytosis and are delivered to neurones," Journal of Controlled Release 137 (2009) 78-86.

Ulbrich, et al., "Transferrin- and transferrin-receptor-antibody-modified nanoparticles enable drug delivery across the blood-brain barrier (BBB)," European Journal of Pharmaceutics and Biopharmaceutics 71 (2009) 251-256.

Pereverzeva, et al., "Intravenous tolerance of a nanoparticle-based formulation of doxorubicin in healthy rats," Toxicology Letters 178 (2008) 9-19.

Kreuter, et al., "Use of nanoparticles for cerebral cancer," Tumori: 9-4: 271-277, 2008.

Kreuter, "Nanoparticles—a historical perspective," International Journal of Pharmaceutics 331 (2007) 1-10.

Petri, et al., "Mechanism of Action and Surfactant Influence During Chemotherapy of Brain Tumour Using Doxorubicin-Loaded Poly(butyl Cyanoacrylate) Nanoparticles," NSTI-Nanotech 2007, vol. 2, 2007, p. 386-389.

Ambruosi, et al., "Influence of surfactants, polymer and doxorubicin loading on the anti-tumour effect of poly(butyl cyanoacrylate) nanoparticles in a rat glioma model," Journal of Microencapsulation, Aug. 2006; 23(5): 582-592.

Ambruosi, et al., "Biodistribution of polysorbate 80-coated doxorubicin-loaded [14C]-poly(butyl cyanoacrylate) nanoparticles after intravenous administration to glioblastoma-bearing rats," Journal of Drug Testing, Feb. 2006; 14(2): 97-105.

Ambruosi, et al., "Body distribution of polysorbate-80 and doxorubicin-loaded [14C]-poly(butyl cyanoacrylate) nanoparticles after i.v. administration in rats," Journal of Drug Targeting, Dec. 2005; 13(10): 535-542.

Schuller et al., "Degradation of microvascular brain endothelial cell β-catenin after co-culture with activated neutrophils from patients undergoing cardiac surgery with prolonged cardiopulmonary bypass," Biochemical and Biophysical Research Communications 329 (2005) 616-623.

Kreuter, "Application of nanoparticles for the delivery of drugs to the brain," International Congress Series 1277 (2005) 85-94.

Kreuter, "Influence of the Surface Properties on Nanoparticle-Mediated Transport of Drugs to the Brain," Journal of Nanoscience and Nanotechnology, 2004, vol. 4, No. 5; p. 484-488.

Kreuter, "Direct Evidence that Polysorbate-80-Coated Poly(Butylcyanoacrylate) Nanoparticles Deliver Drugs to the CNS via Specific Mechanisms Requiring Prior Binding of Drug to the Nanoparticles," Pharmaceutical Research, vol. 20, No. 3, Mar. 2003; p. 409-416.

Kreuter, "Transport of Drugs Across the Blood-Brain Barrier by Nanoparticles," Curr. Med. Chem.—Central Nervous System Agents, 2002, 2, 241-249.

Kreuter, et al."Apolipoprotein-medicated Transport of Nanoparticle-bound Drugs Across the Blood-Brain Barrier," Journal of Drug Testing, 2002 vol. 10 (4), pp. 317-325.

Gelperina, et al., "Toxicological studies of doxorubicin bound to polysorbate 80-coated poly(butyl cyanoacrykate) nanoparticles in healthy rats and rats with intracranial glioblastoma," Toxicology Letters 126 (2002) 131-141.

Kreuter, "Nanoparticulate systems for brain delivery of drugs," Advanced Drug Delivery Reviews 47 (2001) 65-81.

Ramge, et al., "Polysorbate-80 coating enhances uptake of polybutylcyanoacrylate (PBCA)-nanoparticles by human and bovine primary brain capillary endothelial cells," European Journal of Neuroscience, vol. 12, pp. 1931-1940 (2000).

Ramge, et al., "Circadian Phase-dependent Antinociceptive Reaction in Mice and the Tail-flick Test after Intravenous Injection of Dalargin-Loaded Nanoparticles," Chronobiology International, 16(6), 767-777 (1999).

Alyautdin, et al., "Drug delivery to brain by nanoparticles," (2003) eksperimental'naya i Klinicheskaya Farmakologiya, 66 (2), pp. 65-68.

Balali-Mood Md Phd, et al., "Neurotoxic Disorders of Organophosphorous Compounds and Their Managements," Arch Iranian Med 2008; 11 (1): 65-89.

Kuca, et al., "Preparation of Oxime HI-6 (Dichloride and Dimethanesulphonate)- Antidote against Nerve Agents," Defense Science Journal, vol. 58, No. 3, May 2008, pp. 399-404.

Antonijevic et al., "Unequal Efficacy of Pyridinium Oximes in Acute Organophosphate Poisoning," Clinical Medicine & Research, vol. 5, No. 1: 71-82, 2007.

Chambers, et al., "Development of a broad-spectrum Oxime for the treatment of nerve agent toxicity,", 2006.

Kuca, et al., "In Vitro Reactivation Potency of Acetylcholinesterase Reactivators—K074 and K075—to Reactivate Tabun-inhibited Human Brain Cholinesterases," Neurotoxicity Research, 2007, vol. 11(2), pp. 101-106.

Dennison, et al. "Corticosteroids in rheumatoid arthritis," British Medical Journal vol. 316, pp. 789-790 (1998).

(56) References Cited

OTHER PUBLICATIONS

KENAGOG® CREAMSTriamcinolone Acetonide Cream USPO. 025%, 0.1 %,0.5% (Online) http://dailymed.n1m.nih.gOYdailymed/fda/fdaDrugXsl.cfm?id=1872&type=display; retrieved Jun. 21, 208 (8 pages).

D. Farcasiu, et al. "Evaluation of hydrogen bonding by C-13NMR" Catalysis Letters 31 (1995) 351-358.

Chemistry and Industry; Applied Chemistry; Nigel Freestone; Nov. 7, 2005 (4 pgs).

Chemistry and Industry; New Drug Delivery Systems; Alexander T. Florence; Dec. 20, 1993 (7 pgs).

Advanstar Communications, Inc.; Pharmaceutical Technology; Vivek Kharb; Meenakshi Bhatia; Harish Dureja; Deepak Kaushik; Feb. 1, 2006 (11 pgs).

Advanstar Communications, Inc.; Pharmaceutical Technology Europe; Magdalene Radtke; Eliana B. Souto; Rainer H. Muller; Apr. 1, 2005 (4 pgs).

International Search Report and Written Opinion dated Nov. 23, 2009 issued in related International Patent Application No. PCT/US0959386.

U.S. Office Action dated Dec. 9, 2010 issued in related U.S. Appl. No. 11/555,995.

U.S. Office Action dated Mar. 11, 2011 issued in related U.S. Appl. No. 12/245,450.

U.S. Office Action dated May 25, 2011 issued in related U.S. Appl. No. 12/192,400.

Munavalli, et al; Preparation and Properties of Methylenebispyridinium Derivatives; Heterocycles 1986, vol. 24. No. 7; pp. 1883-1892.

U.S. Office Action dated Jun. 22, 2011 issued in related U.S. Appl. No. 12/047,988.

U.S. Office Action dated Aug. 15, 2011 issued in related U.S. Appl. No. 11/555,995.

Luo, et al., "Development of a broad-spectrum Oxime for the treatment of nerve agent toxicity," Conference paper, Division of Biochemistry, Walter Reed Army Institute of Research, Silver Spring, MD 20910, Report Date: Nov. 2006 Report No. A376184. Available at http://www.dtic.mil/cgi-bin/GetTRDoc?Location=U2&doc=GetTRDoc.pdf&AD=ADA481673, retrieved on Mar. 9, 2011.

Alyautdin, et al, "Drug delivery to brain by nanoparticles," (2003) eksperimental'naya i Klinicheskaya Farmakologiya, 66 (2), pp. 65-68. English language Abstract can be found on p. 68, final paragraph.

Digiovanni, Jr., M.D., Cleto, Domestic Terrorism With Chemical or Biological Agents: Psychiatric Aspects, Am J Psychiatry, Oct. 1999, pp. 1500-1505, vol. 156:10.

D'Mello, G.D., Behavioural Toxicity of Anticholinesterases in Humans and Animals—A Review, Human & Experimental Toxicology, 1993, pp. 3-7, vol. 12.

Eyer, et al., Oximes—Chapter 15, Chemical Warfare Agents: Toxicology and Treatment, 2007, pp. 305-329, 2nd Edition.

Garcia, et al., Sensitive and Rapid Blood and Tissue HPLC Oxime Assay and Pharmacokinetics of MMB-4 in Guinea Pigs and African Green Monkeys, 2006.

International Search Report and Written Opinion dated Jul. 17, 2009 issued in PCT Patent Application No. PCT/US09/35539, 8 pages.

International Search Report and Written Opinion dated Oct. 6, 2009 issued in PCT Patent Application No. PCT/US09/52457, 9 pages.

Jager, et al., Toxicity of Diacetyl Monoxime and of Pyridine-2-Aldoxime Methiodide in Man, Bull John Hopkins Hosp., 1958, pp. 203-211, vol. 102.

Jamal, Goran A., Long term neurotoxic effects of organophosphate compounds, Adverse Drug React. Toxicol. Rev, 1995, pp. 85-99, vol. 14(2).

Luo, et al., An In Vitro Comparative Study on the Reactivation of Nerve Agent-Inhibited Guinea Pig and Human Acetylcholinesterases by Oximes, Biochemistry, 2009, pp. 11771-11779, vol. 46.

Marrs et al., Chemical Warfare Agents: Toxicology and Treatment Second Edition, 2007, pp all. Table of contents attached electronically, physical book mailed to USPTO Oct. 8, 2010.

McDonough, et al., Behavioral Correlates of Soman-Induced Neuropathology: Deficits in DRL Acquisition, Neurobehavioral Toxicology and Teratology, 1986, pp. 179-187, vol. 8.

U.S. Office Action dated Jun. 25, 2008 issued in U.S. Appl. No. 11/555,995, 23 pages.

U.S. Office Action dated Nov. 28, 2008 issued in U.S. Appl. No. 11/555,995, 23 pages.

Giulian et al, "Short Communication", Optical and Quantum Electronics, vol. 9, pp. 263-264; 1977.

Patani et al, "Bioisosterism: A Rational Approach in Drug Design", (Chemical Reviews, vol. 96, No. 8, pp. 3147-3176; 1996.

U.S. Office Action dated Nov. 1, 2011 issued in related U.S. Appl. No. 11/555,995.

European Supplementary Search Report—mailing date Sep. 27, 2011, issued in related European Appln. No. 09718843.7.

Sevelova et al, "Antidotal Treatment of GF-agent intoxication in mice with bispyridinium Oximes", Toxicology, vol. 207, No. 1, pp. 1-6, 2005.

Aurbek et al, "Analysis of Inhibition, Reactivation and Aging Kinetics of Highly Toxic Organophosphorus Compounds with Human and Pig Acetylcholinesterase", Toxicology, vol. 224, No. 1-2. pp. 91-99, 2006.

Office Action dated Dec. 29, 2011 issued in related U.S. Appl. No. 12/047,988.

Office Action dated Nov. 29, 2011 issued in related U.S. Appl. No. 12/245,450.

Office Action dated Jan. 26, 2012 issued in related U.S. Appl. No. 12/192,400.

Thiermann, "HI 6 dimethanesulfonate has better dissolution properties than HI 6 dichloride for application in dry/wet autoinjectors," International Journal of Pharmaceutics vol. 137, Issue 2, Jun. 28, 1996, pp. 167-176.

European Search Report dated Oct. 31, 2011 issued in related European Patent Application No. 09807064.2.

Office Action dated May 20, 2014 issued in related U.S. Appl. No. 11/555,995 (15 pgs).

Office Action dated Sep. 14, 2012 issued in related U.S. Appl. No. 12/047,988 (15 pgs).

Office Action dated Oct. 11, 2012 issued in related U.S. Appl. No. 12/192,400 (28 pgs).

Office Action dated Oct. 19, 2012 issued in related European Patent Application No. 09 718 843.7 (4 pgs).

Office Action dated Jan. 20, 2013 issued in related Israel Patent Application No. 208084 (3 pgs.).

J.C. Chaumeil, "Micronization: A Method of Improving the Bioavailability of Poorly Soluble Drugs", Methods and Findings in Experimental and Clinical Pharmacology, Apr. 1998, vol. 20, No. 3, pp. 211-215.

W.S. Choi, et al, "Amorphous Ultrafine Particle Preparation for Improvement of Bioavailability of Insoluble Drugs: Grinding Characteristics of Fine Grinding Mills"; International Journal of Mineral Processing, vol. 74, Supplement 1, Dec. 10, 2004, pp. S165-S172.

R.C. Garner et al, "Comparison of the Absorption of Micronized (Daflon 500 mg) and Nonmicronized 14C-Diosmin Tablets After Oral Administration to Healthy Volunteers by Accelerator Mass Spectrometry and Liquid Scintillation Counting"; Journal of Pharmaceutical Sciences, Jan. 2002, vol. 91, Issue 1, pp. 32-40.

\* cited by examiner

NANOPARTICLES FOR DRUG DELIVERY TO THE CENTRAL NERVOUS SYSTEM

GOVERNMENT RIGHTS CLAUSE

This invention was made with United States Government support under Contract No. W9113M-05-C-0199 awarded by the United States Army. The Government has certain rights in this invention.

FIELD OF THE INVENTION

The present invention relates to nanoparticle formulations to provide relatively more rapid delivery of such particles across the blood brain barrier. Such formulations may therefore be relied upon for treatment of exposure to cholinesterase inhibitors, such as phosphorous containing cholinesterase inhibitor type compounds.

BACKGROUND

Stimulating signals are typically carried by acetylcholine within a nervous system synapse. Such signals may be discontinued by a specific type of cholinesterase enzymes, acetylcholinesterase, which breaks down acetylcholine. If cholinesterase inhibiting chemicals are present, they may then prevent the breakdown of acetylcholine thereby disrupting normal nervous system activity. For example, certain chemical classes of pesticides, such as organophosphates and carbamates, may result in toxic cholinesterase inhibition. Accordingly, if an individual is regularly exposed to such inhibitors, there remains a need to prophylactically or therapeutically treat such toxicity. Among other things, individuals or animals who may have been exposed to a carbamate type cholinesterase inhibitor may currently be treated with atropine, and those exposed to organophosphates may beneficially be treated with a pralidoxime antidote.

Nanotechnology focuses on the development of new materials, devices and systems that typically involves the formation of particles on the nanometer length scale. To date, a number of techniques have been developed, e.g. mechanical grinding and the formation of particles of a desired size, as well as certain chemical techniques that may rely upon controlled precipitation from a given liquid medium. Relatively intense research into nanotechnology has recently led to potential applications, such as the formation of particles engineered to carry a variety of substances in a controlled and targeted manner for drug delivery.

SUMMARY

In a first exemplary embodiment, the present disclosure relates to a method for forming nanoparticles for transport across the blood-brain barrier, comprising combining a bis-quarternary pyridinium aldoxime salt with a liquid medium, wherein said liquid medium comprises a hydrophilic or hydrophobic media. This may then be followed by milling the combination of the bis-quaternary pyridinium aldoxime salt in the liquid medium wherein the bis-quaternary pyridinium aldoxime salt is milled to a largest size dimension of 1 nm to 999 nm. One may then follow with the step of administering such nanoparticles to a mammal in a manner which allows the particles to enter the bloodstream whereby the nanoparticles cross the blood-brain barrier In another exemplary embodiment the present disclosure relates to a composition comprising a bis-quarternary pyridinium aldoxime salt in a liquid medium, wherein the liquid medium comprises a hydrophilic or hydrophobic media and wherein the bis-quaternary pyridinium aldoxime salt is a milled salt with a largest size dimension of 1 nm to 999 nm.

In another exemplary embodiment the present disclosure relates to a nanoparticle for transport across the blood-brain barrier, comprising a polymeric resin containing secondary bonding capability sufficient to absorb a bis-quaternary pyridinium-2-aldoxime salt of the formula:

$$HO-N=CH-\underset{R^-}{\overset{}{C_5H_4N^+}}-CH_2-\underset{R^-}{\overset{}{N^+C_5H_4}}-CH=N-OH$$

wherein the nanoparticle has a largest size dimension of 1 nm to 999 nm and $R^-$ refers to an anionic counterion for the cationic charge associated with the nitrogen.

In another exemplary embodiment the present disclosure relates to a nanoparticle for transport across the blood-brain barrier, comprising a polymeric resin, wherein said polymer resin encapsulates a bis-quaternary pyridinium-2-aldoxime salt of the formula:

$$HO-N=CH-\underset{R^-}{\overset{}{C_5H_4N^+}}-CH_2-\underset{R^-}{\overset{}{N^+C_5H_4}}-CH=N-OH$$

wherein the nanoparticle has a largest size dimension of 1 nm to 999 nm and $R^-$ refers to an anionic counterion for the cationic charge associated with the nitrogen.

DETAILED DESCRIPTION

Figure 1:
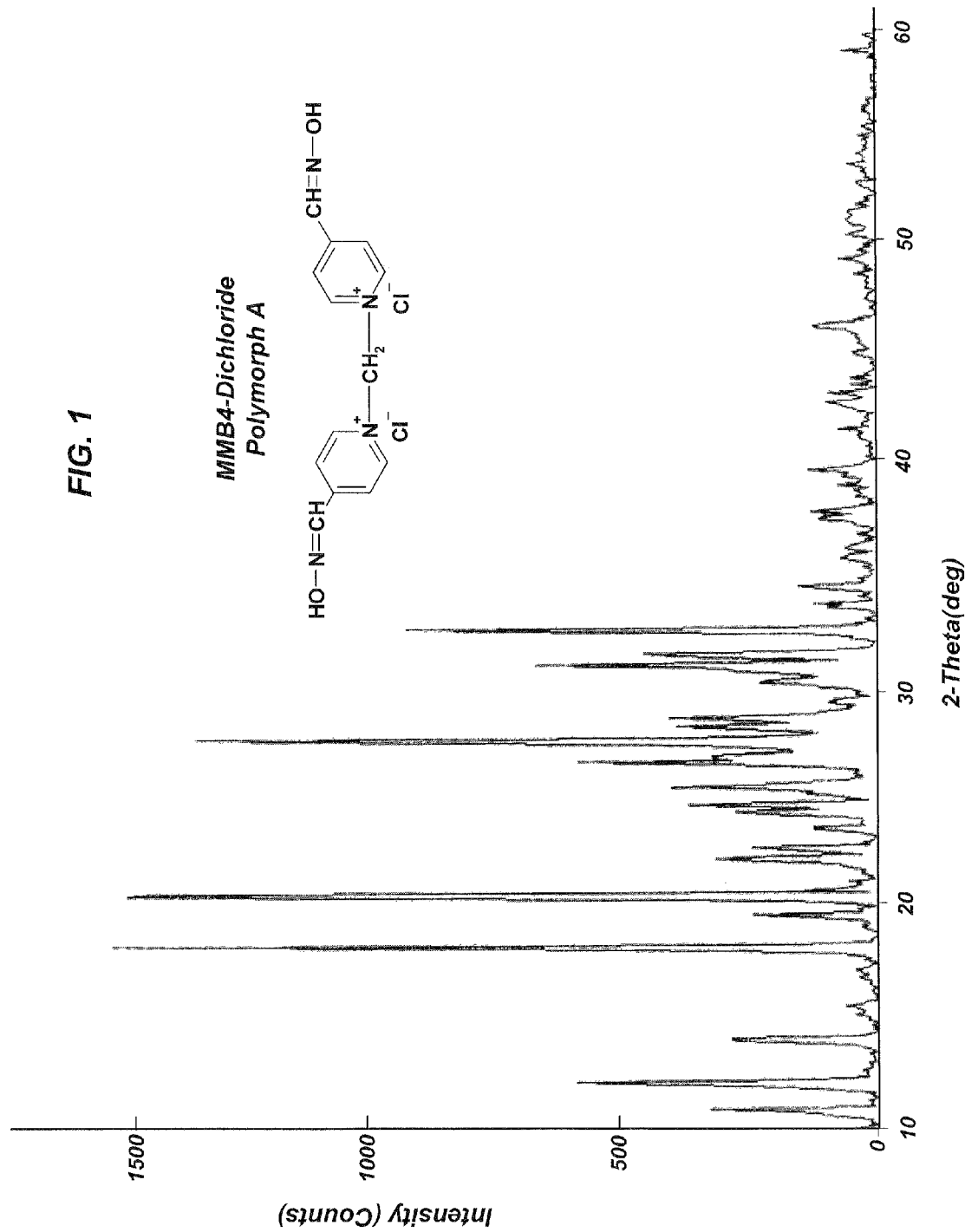
FIG. 1 is an X-ray diffraction pattern for MMB4-Dichloride Polymorph A.

It is to be understood that the invention is not limited in its application to the details of construction and the arrangement of components set forth in the following description or illustrated in the drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

The present disclosure is directed at nanoparticles for drug delivery, which may be understood as a nanodelivery drug complex, including one or more particles that are less than one micron (1.0 μm) in a largest dimension. Accordingly, the nanoparticles herein may have a largest size dimension of 1 nm to 999 nm, including all values and increments therein, such as between 1-900 nm, 1-800 nm, 1-700 nm, etc., in 1 nm increments. Furthermore, the nanoparticles herein may specifically have a largest size dimension of 50-400 nm, or 100-300 nm, or 190-210 nm, including all values and increments therein in 1 nm increments. Preferably, the nanoparticles may have a size in the range 10 nm to 300 nm.

Accordingly, there are several strategies disclosed herein with respect to the design of a nanoparticle formulation to facilitate transport across the blood brain barrier (BBB). It is therefore contemplated herein that the nanodelivery-drug complex will be administered systemically (for example, intravenously) and would locate the central nervous system (CNS) while producing relatively minimal systemic effects and be able to target and cross the BBB and enter the CNS, and then carry out its primary active function, such as releasing a drug.

There are also several drug complexes that may be utilized herein in nanoparticulate form to prophylactically and/or therapeutically treat intoxication in a person or animal due to the presence of a cholinesterase inhibitor, such as a phosphorous cholinesterase inhibitor. The nanodelivery-drug complexes may, e.g., generally utilize bis-quaternary pyridinium aldoxime salts to prophylactically and/or therapeutically treat intoxication in a person or animal due to the presence of a cholinesterase inhibitor, such as a phosphorous containing cholinesterase inhibitor.

Such bis-quaternary pyridinium aldoxime salts may specifically include 1,1'methylenebis[4-(hydroxyimino)methyl]-pyridinium salt, which may be represented by the following formula:

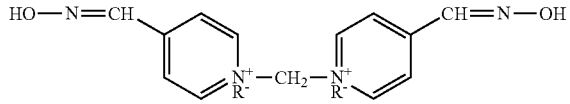

where R⁻ may be a halide counteranion such as a halogen (e.g. Cl⁻ or Br⁻ or I⁻) in which case the compound may be referred to as "MMB4 Dihalide". More generally, R may be derived from a salt of an inorganic or organic acid. For example, the anion may be derived from hydrogen sulfate ($H_2SO_4$), nitrate, fumarate, lactate, tartate, citrate, and/or acetate.

In addition, R⁻ may be a counteranion such as an alkyl sulfonate group. In such a case, the 1,1'-methylenebis[4-(hydroxyimino)methyl]-pyridinium salt would assume the following general formula:

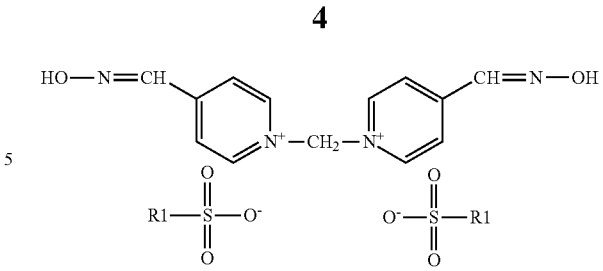

wherein R1 may be selected such that it does not interfere (e.g. steric interference) with the formation of the particular polymorphic pyridinium salts noted below. Accordingly, R1 may be a methyl (—$CH_3$) group, and it is contemplated herein that it may also include ethyl type group functionality (—$CH_2CH_3$).

One particularly useful and convenient synthetic procedure for the formation of the pyridinium salts may involve the preparation of 1,1'-methylenebis[4-[(hydroxyimino)methyl]-pyridinium] diodide hereinafter referred to as "MMB4 DI", which may then be converted to 1,1'-methylenebis[4-[(hydroxyimino)methyl]-pyridinium] dimethanesulfonate "MMB4 DMS." This synthetic procedure is outlined in the general reaction scheme illustrated below:

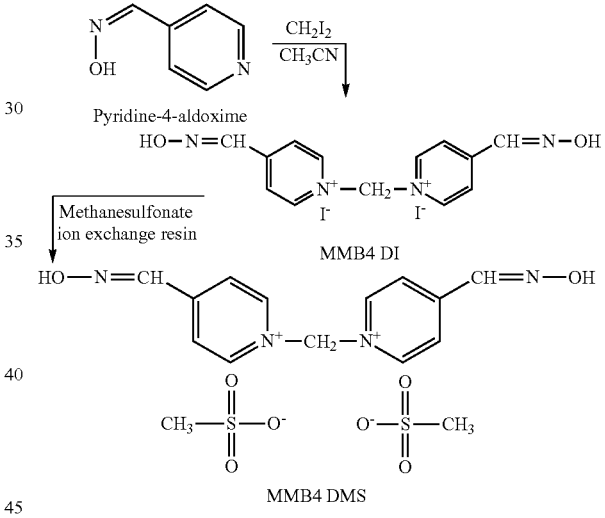

In addition, it may be appreciated that the MMB4 DI may be converted, again by the convenient procedure of ion exchange, to a particular dihalide salt, such as the dichloride salt, as illustrated below:

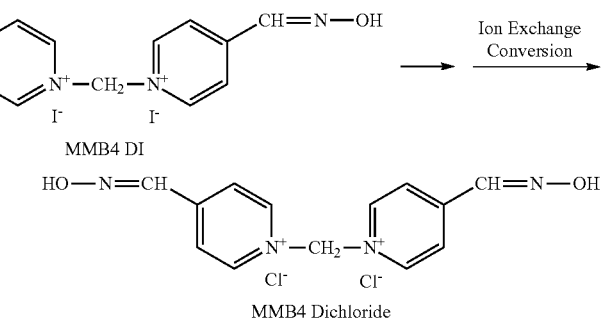

As noted in U.S. application Ser. No. 12/047,988 the MMB4 dichloride and/or the MMB4 DMS compounds may now be isolated in one of two polymorphic forms by control of, e.g., the solvents that may be employed for the pyridinium salt recrystallization. In addition, such polymorphic forms provide the ability to offer improved prophylactic or therapeutic treatment of a person or animal intoxicated with a cholinesterase inhibitor. Accordingly, attention is therefore next directed to FIG. 1, which provides the x-ray diffraction pattern [intensity (counts) versus 2-Theta(degrees)] for the MMB4 dichloride compound in the form of what is now termed MMB4-dichloride Polymorph A. The diffraction patterns (as well as the other diffraction patterns reported herein) were made on a Siemens Kristalloflex 805 with a model D500 goniometer, serial number WM80030464X. The diffraction patterns were then processed using JADE v3.1 from Materials Data, Inc (program serial number MDI-R95704. In general, a representative portion of the sample for analysis was ground to a grain size of less than 25 microns and then spread on a polycarbonate specimen holder. The x-ray tube was run at 40 kV and 30 mA with a 2-theta range of 10-60 degrees. The instrument may be calibrated at regular intervals using appropriate standards.

As can be seen from FIG. 1, the MMB4 dichloride compound in the form of polymorph A herein indicates one or more x-ray diffraction peaks with relative intensity counts (artificial units) between 500-1500 at the 2 Theta angles of between 10-35 degrees, which relatively intensity counts for the peaks drop to a level of less than 500 counts at 2 Theta angles of greater than about 35 degrees. That is, no peaks are present with relative intensity counts of more than 250 at 2 Theta angles between 35-60 degrees. Accordingly, it may be understood herein that the MMB4 dichloride compound in the form of polymorph A may be characterized as having an x-ray diffraction pattern with distinguishing peaks at the 2 Theta angles of between 10-35 degrees as compared to the non-distinguishing x-ray diffraction peaks at the 2 Theta angles of greater than 35 degrees. By reference to distinguishing peaks, it may be understood (upon consideration of FIG. 1) as those peaks and/or collection of peaks within the 2 Theta angles of 10-35 degrees which then may be employed to provide identifiable d-spacing (Braggs Law) for the MMB4 dichloride polymorph A. Accordingly, reference to a collection of peaks herein may include, e.g. information sourced from 2-100 peaks, including all values and increments within the range of 2-100.

Figure 2:
FIG. 2 is a scanning electron micrograph of MMB4 Dichloride Polymorph A.

Attention is therefore next directed to FIG. 2, which provides a scanning electron micrograph of MMB4 dichloride Polymorph A. As can be seen, MMB4 dichloride Polymorph A may also be characterized as having a needle-like particulate structure, with an aspect ratio (AR) or length divided by largest diameter of greater than 2:1. More particularly, the aspect ratio may be in the range of 2:1 to 16:1, including all values and increments therein.

Figure 3:
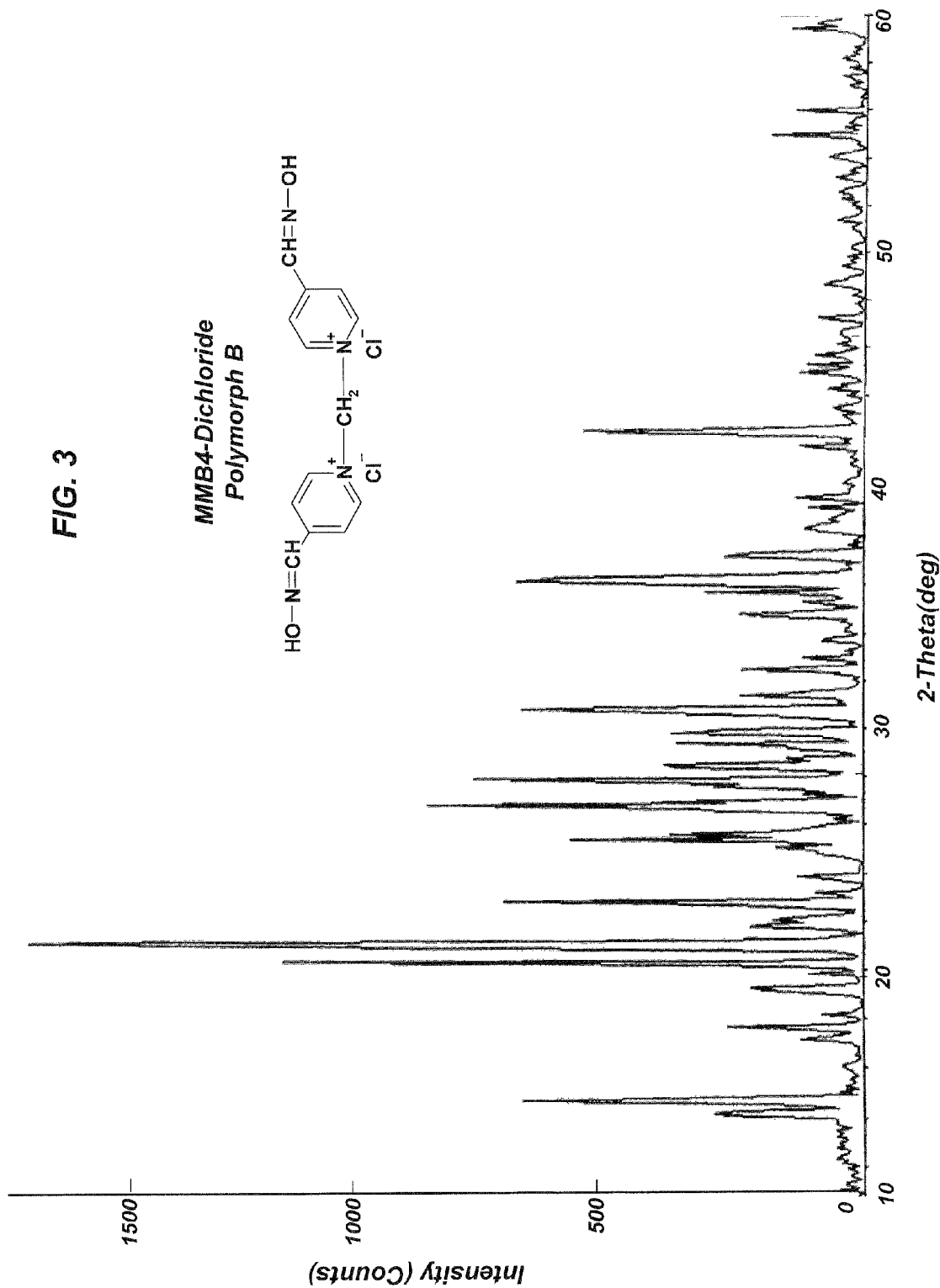
FIG. 3 is an X-ray diffraction pattern for MMB4 Dichloride Polymorph B.

Attention is next directed to FIG. 3, which provides the x-ray diffraction pattern of MMB4 dichloride Polymorph B. As can be seen, MMB4 dichloride Polymorph B indicates one or more x-ray diffraction peaks having relative intensity counts (artificial units) between 500-1500 at the 2 Theta angles of between 10-45 degrees, which relatively intensity counts for the peaks drop to a level of less than 500 counts at 2 Theta angles greater than about 45 degrees. That is, no peaks are present with relative intensity counts of more than 250 at 2 Theta angles between 45-60 degrees. Accordingly, it may be understood herein that the MMB4 dichloride compound in the form of polymorph B may be characterized as having an x-ray diffraction pattern with distinguishing peaks at the 2 Theta angles of between 10-45 degrees as compared to the non-distinguishing x-ray diffraction peaks at the 2 Theta angles of greater than 45 degrees. By reference to distinguishing peaks, it may again be understood (upon consideration of FIG. 3) as those peaks and/or collection of peaks within the 2 Theta angles of 10-45 degrees which then may be employed to provide identifiable d-spacing (Braggs Law) for the MMB4 dichloride polymorph B.

Figure 4:
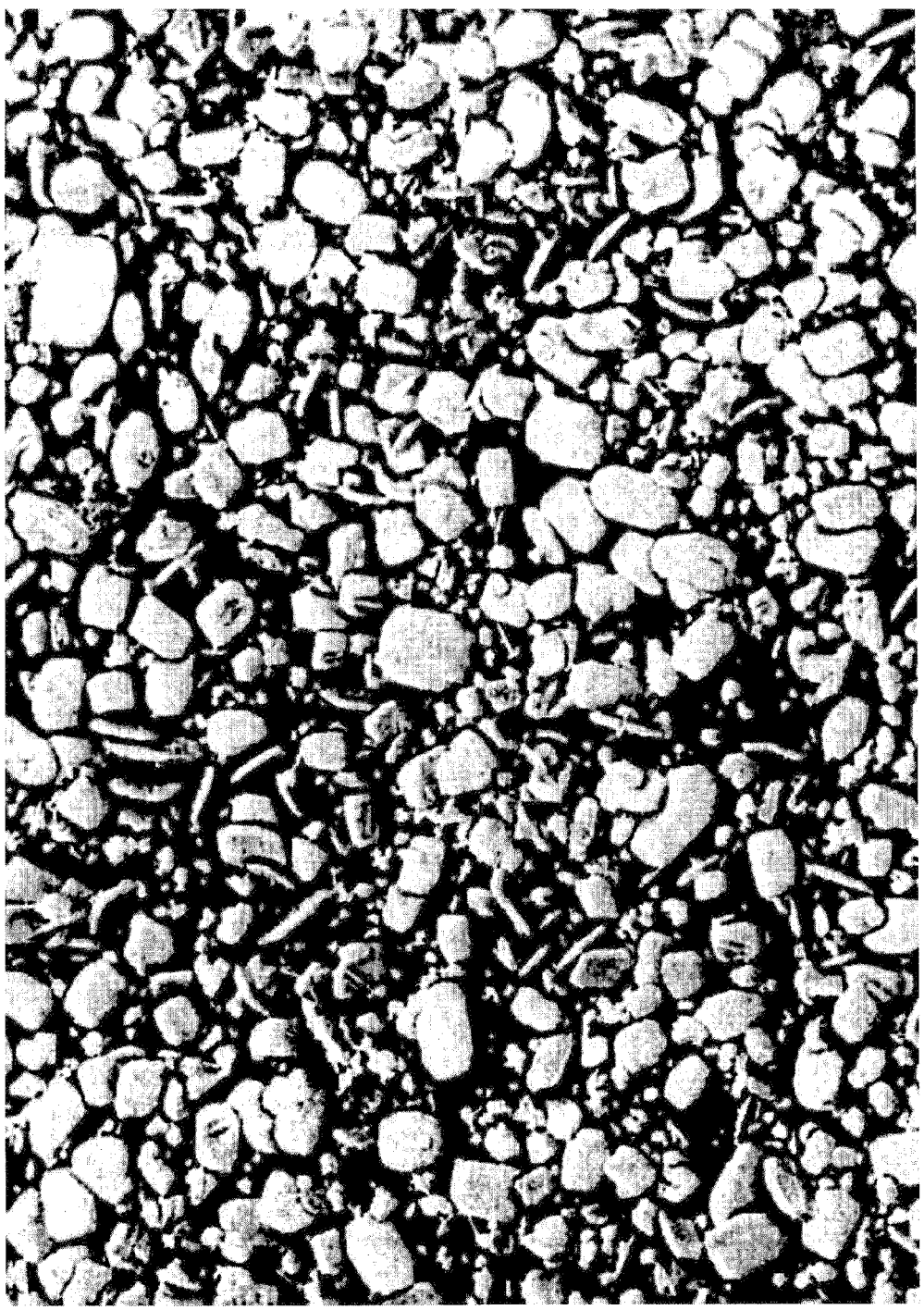
FIG. 4 is a scanning electron micrograph of MMB4 Dichloride Polymorph B.

Attention is therefore next directed to FIG. 4 which provides a scanning electron micrograph of MMB4 dichloride Polymorph B. As can be seen, MMB4 dichloride Polymorph B may also be characterized as having either a particulate structure that is of a square, rectangular, rhomboid (i.e. a parallelogram in which adjacent sides are of unequal lengths) and/or rhombus (a rhomboid with right angled corners) type geometry.

Figure 5:
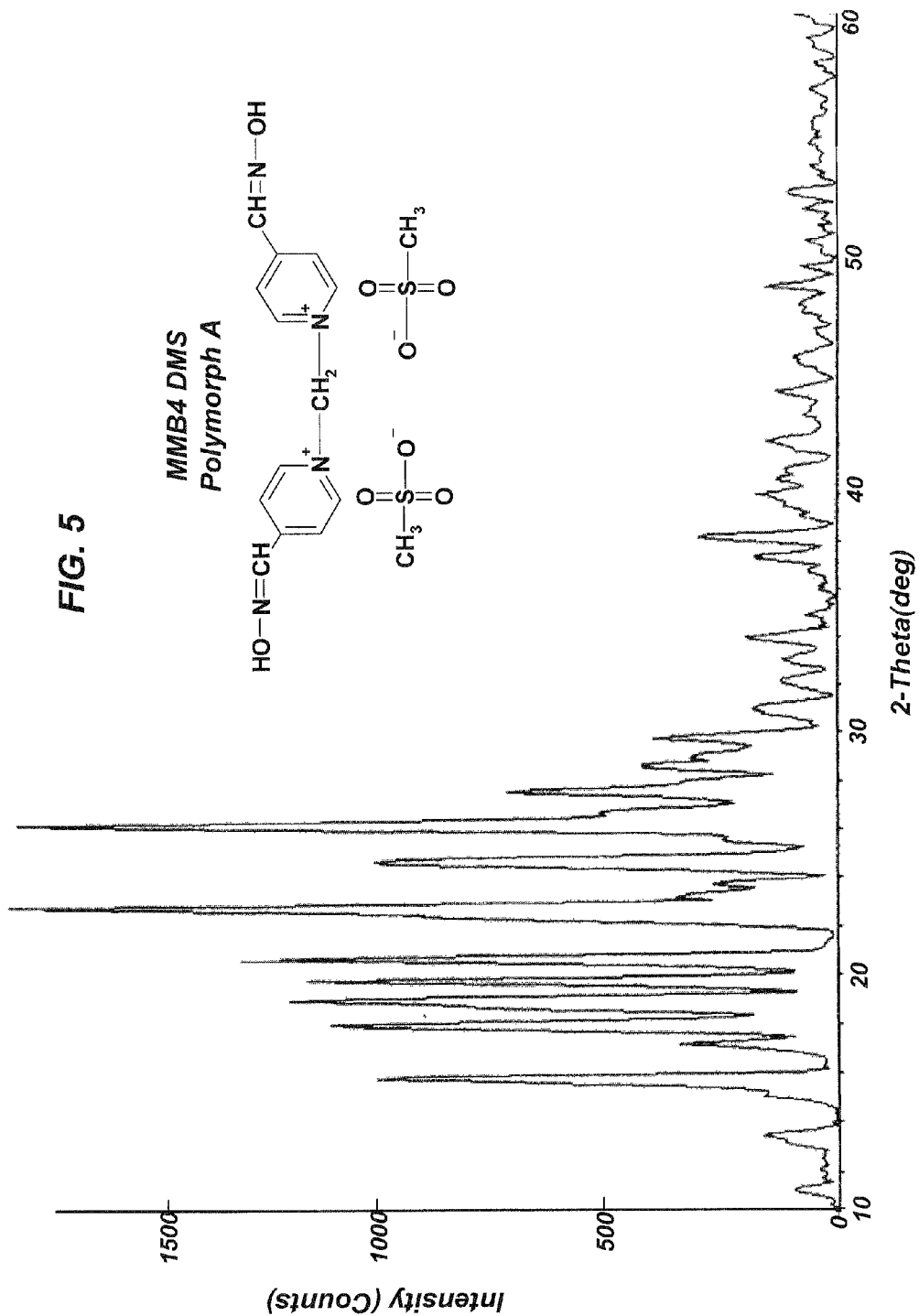
FIG. 5 is an X-ray diffraction pattern for MMB4 DMS Polymorph A.

Attention is next directed to FIG. 5 which provides the x-ray diffraction pattern of MMB4 DMS Polymorph A. As can be seen, MMB4 DMS Polymorph A indicates one or more x-ray diffraction peaks with relative intensity counts (artificial units) between 500-1500 at the 2 Theta angles of between 10-30 degrees, which relatively intensity counts for the peaks drop to a level of less than 500 counts at 2 Theta angles greater than about 30 degrees. That is, no peaks are present with relative intensity counts of more than 250 at 2 Theta angles between 30-60 degrees. Accordingly, it may be understood herein that the MMB4 DMS compound in the form of Polymorph A may be characterized as having an x-ray diffraction pattern with distinguishing peaks at the 2 Theta angles of between 10-30 degrees as compared to the non-distinguishing x-ray peaks at the 2 Theta angles in the range of greater than 30 degrees, e.g. in the range of greater than 30 degrees to about 60 degrees. By reference to distinguishing peaks, it may again be understood (upon consideration of FIG. 5) as those peaks and/or collection of peaks within the 2 Theta angles of 10-30 degrees which then may be employed to provide identifiable d-spacing (Braggs Law) for the MMB4 DMS Polymorph A.

Figure 6A:
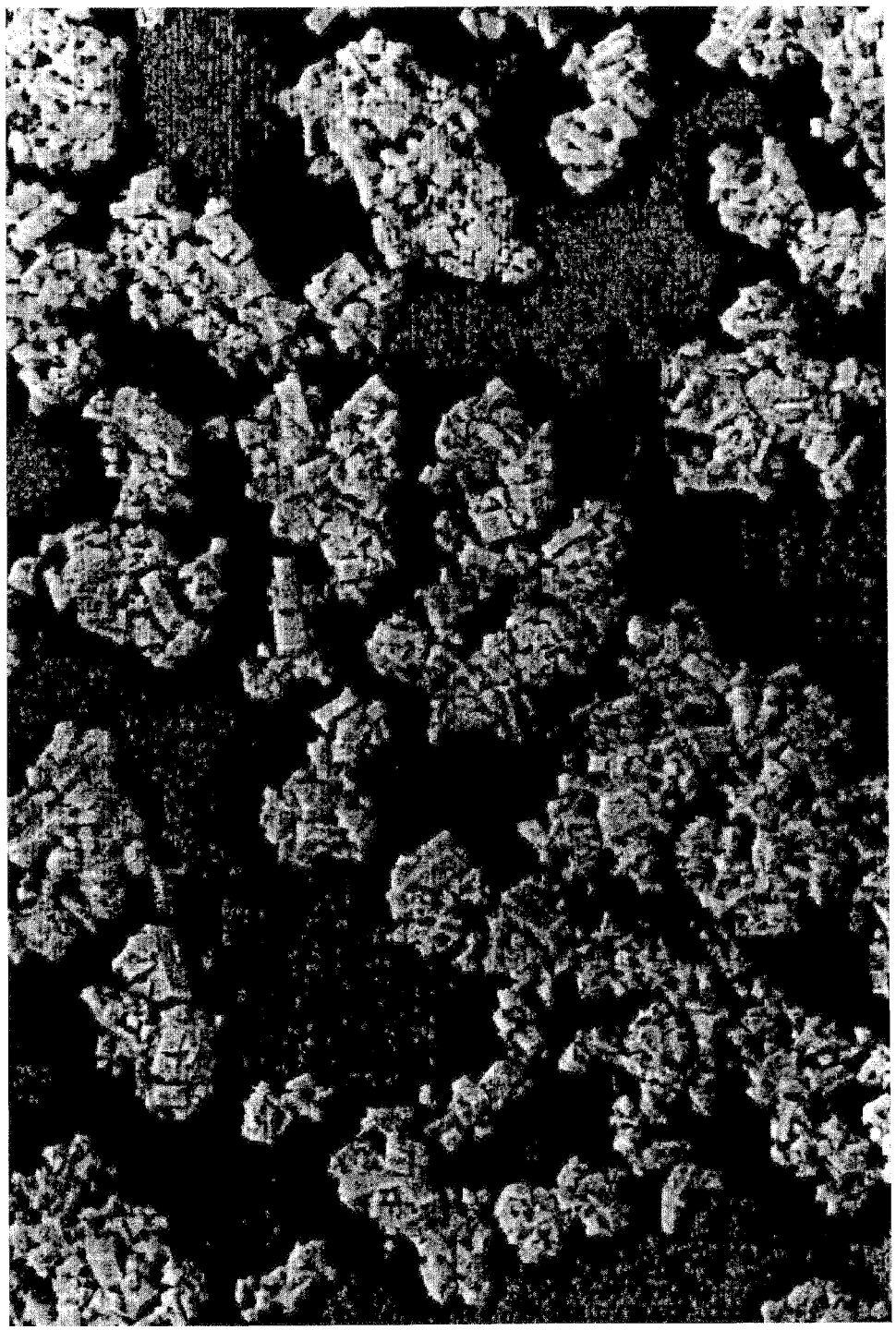
FIG. 6A is a scanning electron micrograph of MMB4 DMS Polymorph A.
Figure 6B:
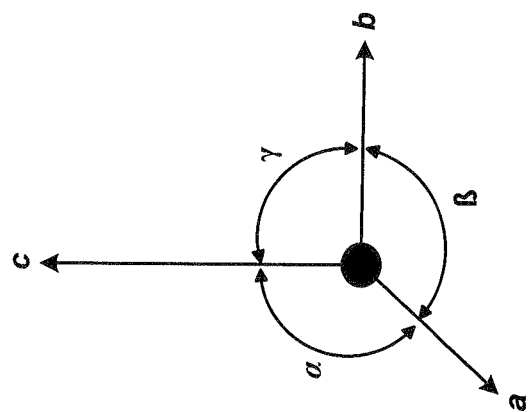
FIG. 6B is an illustration of the crystalline structure of MMB4 DMS Polymorph A identified in FIG. 6A.
Figure 6B:
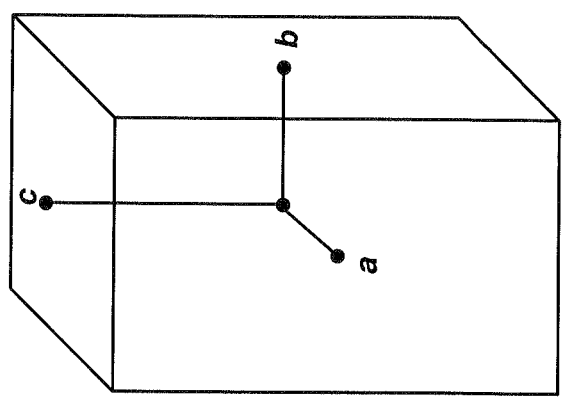

FIG. 6A next provides a scanning electron micrograph of MMB4 DMS Polymorph A. As can be seen, MMB4 DMS Polymorph A may be described as having cubic rectangular type crystal structure or geometry. A cubic rectangular geometry may be understood as a cubic configuration that may be stretched along its (c) axis to provide a rectangular configuration, consisting of three substantially equal or equatorial (a, b and c) axes at 90° (+/−5°) and the c axis is longer than the horizontal axis. See FIG. 6B and angles α, β, and γ which are at 90° (+/−5°).

Figure 7:
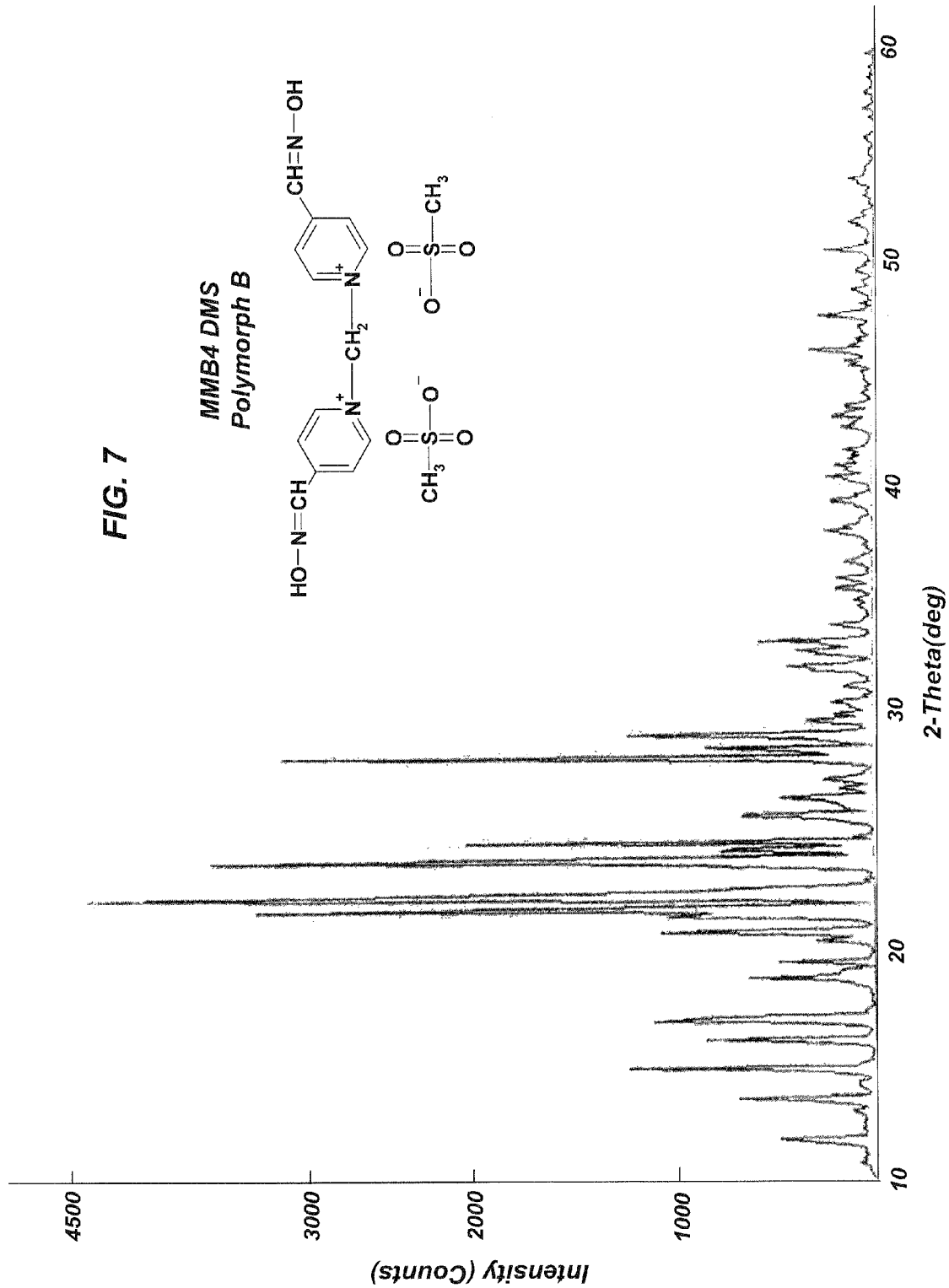
FIG. 7 is an X-ray diffraction pattern for MMB4 DMS Polymorph B.

Attention is next directed to FIG. 7 which provides the x-ray diffraction pattern of MMB4 DMS polymorph B. As can be seen, MMB4 DMS Polymorph B indicates one or more x-ray diffraction peaks with relative intensity counts (artificial units) between 1000-4500 at the 2 Theta angles of between 10-30 degrees, which relatively intensity counts for the peaks drop to a level of less than 500 counts at 2 Theta angles greater than about 30 degrees. That is, no peaks are present with relative intensity counts of more than 500 at 2 Theta angles between 30-60 degrees. Accordingly, it may be understood herein that the MMB4 DMS compound in the form of polymorph B may be characterized as having an x-ray diffraction pattern with distinguishing peaks at the 2 Theta angles of between 10-30 degrees as compared to the non-distinguishing x-ray diffraction peaks at the 2 Theta angles of greater than 30 degrees. By reference to distinguishing peaks, it may again be understood (upon consideration of FIG. 7) as those peaks and/or collection of peaks within the 2 Theta angles of 10-30 degrees which then may be employed to provide identifiable d-spacing (Braggs Law) for the MMB4 DMS polymorph B.

Figure 8A:
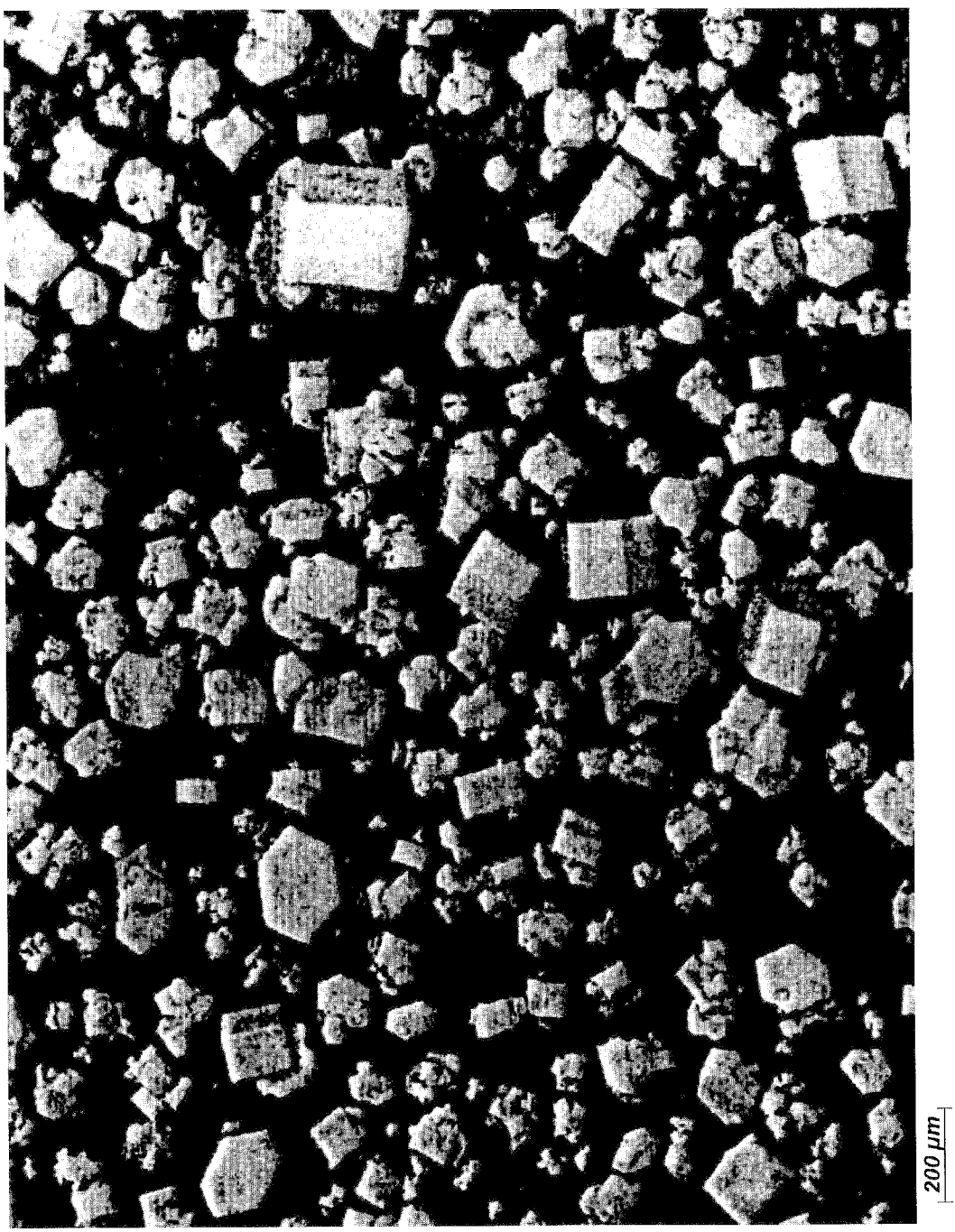
FIG. 8A is a scanning electron micrograph of MMB4 DMS Polymorph B.
Figure 8B:
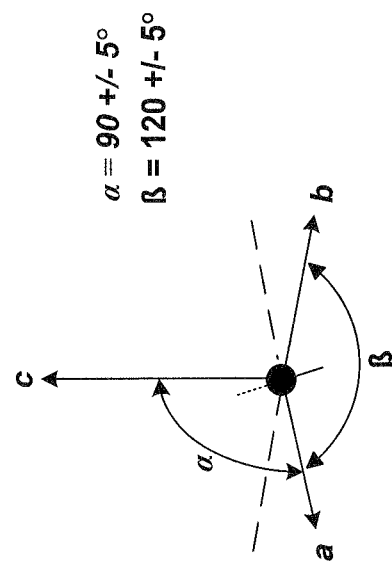
FIG. 8B is an illustration of the crystalline structure of MMB4 DMS Polymorph B identified in FIG. 8A.
Figure 8B:
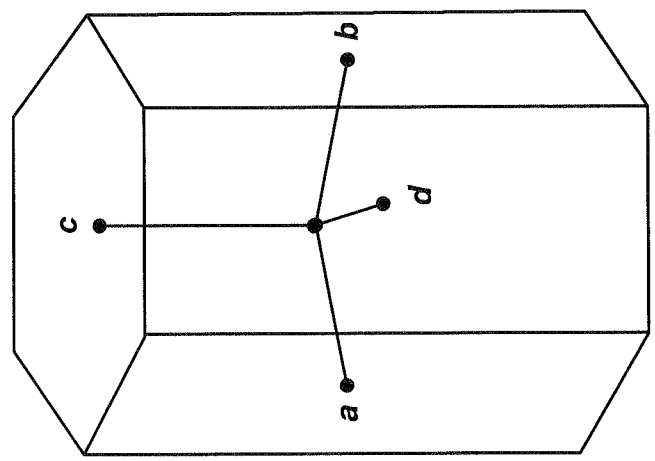

FIG. 8A next provides a scanning electron micrograph of MMB4 DMS Polymorph B. As can be seen, MMB4 DMS Polymorph B may be described as having primarily hexagonal structure. A hexagonal crystal structure may be understood as having four crystallographic axes consisting of three substantially equal or equatorial (a, b, and d) axes at 120° (+/−5°) and one vertical (c) axis that is 90° (+/−5°) to the other three. See, e.g., FIG. 8B, wherein angle α is shown being equal to 120° (+/−5°) and angle β being equal to 90° (+/−5°). The (c) axis may be shorter or longer than the horizontal axis.

Other bispyridinium oximes that may be used herein in any of the indicated embodiments include one or more of the following:

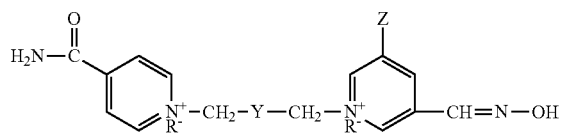

wherein in the above formula, when Y is O and Z is H and where R may be a chloride anion (Cl$^-$) the molecule is knows as HI6-Cl or 1-(2-hydroxyiminomethyl)pyridinium)-3-(4-carbamoylpyridinium)-2-oxapropane dichloride) and where R is a methane sulphonate anion ($CH_3SO_3^-$) the molecule is known as HI6 DMS or 1-(2-(hydroxyiminomethyl)pyridinium)-3-(4-carbamoylpyridinium)-2-oxapropane dimethanesulphonate. When Y is O and Z is —CHNHOH and the R groups amount to an iodide anion (I$^-$) the molecule is known as HLo7 or [(Z)-[1-[4-carbamoylpyridin-1-yl]methoxymethyl]-2-[(Z)-hydroxyiminomethyl]pyridine-4-ylidene]methyl]-oxo-azanium diiodide. Accordingly, in the context of the present disclosure, reference to a bis-quarternary pyridinium aldoxime salt may be understood to include any one or more of: 1. the MMB4 structures noted herein; 2. HI-6 (with a halogen or DMS as the counterion); 3. HLo7; 4. 1,1-[oxybis-(methylene)]bis[4-[(hydroxyimino)methyl]-pyridinium] dichloride sold under the trademark Toxogonin™.

Nanoparticle Formation

The nanoparticles that may be employed herein include the following: (1) polymer based nanoparticles which include some level of attraction and/or which may encapsulate a selected active pharmaceutical ingredient (API) that is intended to cross the BBB and correctly target cells in the CNS; (2) polymer based nanoparticles of the aforementioned type that include specific targeting capability (such as targeting for low density lipoproteins or folic acid receptors) and/or non-specific targeting capability (such as TAT peptide targeting); (3) Surfactant coating of the polymer nanoparticles described in (1) and (2) to enhance transmission across the BBB; (4) nanoparticles of a selected active pharmaceutical ingredient (such as MMB4-Dihalide or MMB4-DMS) that are provided in either hydrophilic or hydrophobic media. Example of hydrophilic media may include polyethers such as polyethylene oxide (PEG) with molecular weights of up to about 20,000 g/mole. In addition, the hydrophilic media may include organic alcohols, such as alkyl alcohols, and more specifically, ethanol. The hydrophobic media may include vegetable oils which are derived from plants and which are liquids at room temperature and are composed of triglycerides. Other hydrophobic media include organic media, more specifically bicyclic compound such as decahydronapthalene, and more specifically, substituted decahydronapthalene compounds such as perfluoro-decahydronapthalene. In addition, hydrophobic media may include polysorbate (e.g. polysorbate 80 such as TWEEN™ 80 or $C_{64}H_{124}O_{26}$) which may be understood as a derivative from polyethoxylated sorbitan and oleic acid. Such nanoparticles directly formed from the indicated active pharmaceutical ingredient and prepared in the indicated hydrophilic or hydrophobic media may also be optionally coated with a surfactant, to again, enhance transmission through the BBB.

Polymer Based Nanoparticles

A. Nanoparticles with Secondary Bonding Interactions to an API

As noted, one may prepare polymer based nanoparticles which include some level of attraction to a selected API, such as the bis-quarternary pyridinium-aldoxime salts noted herein. Such attraction may be understood as a secondary bonding type interaction (a bonding interaction other than a covalent bond). For example, one may prepare a polymeric resin in nanoparticle form that includes a level of electrostatic or polar attraction to a selected API, such that the API is absorbed on the polymeric nanoparticle surface. The level of absorption may be in the range of 0.1-50.0% by weight, including all values and increments therein, in 0.1% increments. The level of absorption may preferably be in the range of 10% by weight to 25% by weight. Such nanoparticles may be conveniently prepared by an emulsion polymerization procedure wherein the selected monomer is polymerized in a water environment utilizing emulsifying agents and water soluble polymerization initiators.

That is, the polymer includes a combination of pendant functional groups attached to the main chain that may provide a net positive and/or negative charge along the length of the chain. Understanding that the MMB4-Dihalide or MMB4-DMS are pyridinium salts, the polymer contemplated herein may have the following general structure to facilitate the formation of secondary bonding (non-covalent) bonding, such as dipole-dipole interaction, with such salts:

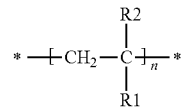

In the above formula, it may be appreciated that R1 and/or R2 may comprise a functional group that provides partial negative polarity to thereby facilitate attraction to the pyridinium salt. For example, R1 and/or R2 may comprise a carbonyl group such as a carboxylate group (—COOH), a nitrile group, an amide group or a hydroxyl group. In such regard, when one of the groups provide a sufficient polarity, the other group may be a hydrogen or alkyl group or aromatic type group. Examples of other polymers include poly(lactic acid), poly(glycolic acid) and copolymers thereof including, e.g., PGA and/or PLA as a block copolymer with PEG, polyanhydrides, polyorthoesters, and polyphosphazines. These are all available commercially or can be manufactured by standard techniques.

For example, one may utilize a cyanoacrylate type polymer of the following general structure:

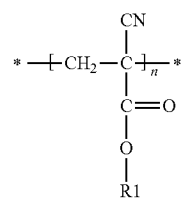

wherein R1 may be an alkyl type group (e.g. —$CH_3$, —$CH_2$—$CH_3$) and/or an aromatic type group and/or a substituted aromatic group. The poly(alkyl cyanoacrylate) nanoparticles may be preferably prepared by an emulsion polymerization of the corresponding monomer wherein the size of the particles formed may be, as noted above, be defined by a largest size dimension of 1 nm to 999 nm. As may then be appreciated, the cyano group may present a partial polarity across the nitrile functionality (δ+ CN δ−) and the carbonyl group may present a similar dipole across the carbonyl (δ+ C═O δ−). That being the case, it may now be appreciated that one may associate the above referenced poly(alkyl cyanoacrylate) with the bis-quaternary pyridinium-aldoxime compounds, as the bis-quarternary nitrogen with a net positive charge will tend to be associated with the above indicated regions of negative charge within the poly(alkyl cyanoacrylate) polymer. This may be illustrated below, which identifies the positive charge on the bis-quarternary nitrogen associated with the partial negative charge on the carbonyl oxygen of the poly(alkyl cyanoacrylate):

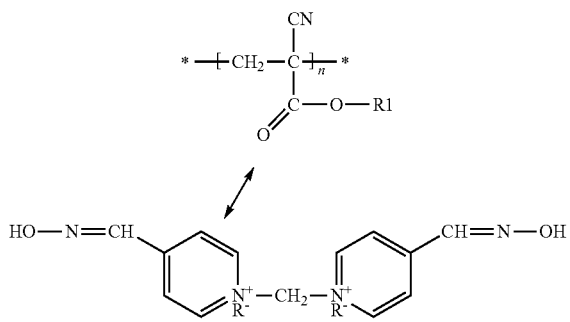

B. Nanoparticles Encapsulating the API

The polymer based nanoparticles may also be configured such that they encapsulate the API. Such may be achieved by polymerization of the selected monomer in the presence of the API which thereby will entrap the API inside the polymeric nanoparticles that are formed. The size of the particles so formed may be defined by a largest size dimension of 1 nm to 999 nm. For example, in the emulsion polymerization, the API (e.g. any of the bis-quaternary pyridinium-aldoxime compounds noted herein) may be included within the polymerizing micelle. Moreover, it may be appreciated that the polymer based nanoparticles may include both of the above capabilities, i.e. the ability to attract the API to the surface as well as the ability to encapsulate the API within the nanoparticle, to thereby increase the level of API transport.

C. Polymer Based Nanoparticles Including Specific and Non-Specific Targeting Capability The aforementioned polymer based nanoparticles may also include specific targeting as well as non-specific type targeting chemistries, as well as a combination of such targeting protocols. For example, the specific targeting protocol may preferably focus on targeting receptors for low density lipoproteins (LDL and/or folic acid receptors). To achieve specific targeting utilizing LDL receptors, apolipoproteins which may be understood herein as proteins that belong to fats or lipids [ApoB protein] may be coated on the surface of the nanoparticles (e.g. the MMB4 dihalide encapsulated in a polymeric nanoparticle). Apolipoproteins will bind to LDL receptors on the surface of the BBB. ApoB protein molecules can be conjugated to the surface of the polymeric nanoparticles using hetero-bi-functional crosslinking. The advantage of this process is that the BBB has a significant density of LDL receptors and may therefore provide relatively more efficient delivery of the nanoparticles across the BBB. The apolipoprotein may be present on the surface of the particles at a level of 0.5-10% by weight.

To achieve specific targeting using folate receptors, one may provide polymeric nanoparticles with folic acid molecules on the surface, which may be present at a level of 0.5% to 10.0% by weight. For example, one may provide a polymeric nanoparticle that may provide for the ability for the covalent attachment of folic acid on the polymeric nanoparticle surface, through the reaction of the folic acid carboxylic group (—COOH) with a pendant organic base group on the polymeric resin forming the nanoparticle. The advantage of this approach is that folic acid being a relatively small molecule, does not significantly alter the size of the nanoparticles. In addition, one may regulate the number of folic acid molecules on the surface of the nanoparticle. Finally, folic acid molecules may be conjugated using EDC chemistry.

Non-specific targeting of the polymeric nanoparticles may include the Tat based targeting approach for cellular drug delivery. Tat is reference to an amino-terminal domain, a cysteine-rich domain, a core region and a basic domain, which may be present on the particles herein at a level of 0.5% to 10.0% by weight. The core domain is a stretch of eleven amino acids between the cysteine-rich and basic domain. The core domain is conserved in all HIV isolates. Tat peptide conjugated nanoparticles may then provide more efficient delivery across the BBB. One advantage of this approach is the relative ease of conjugation of small peptide molecules on the targeted polymeric nanoparticle.

Furthermore, such polymer particles, once associated with a selected API and/or encapsulating a selected API, and/or those including specific targeting and/or general targeting functionality, may be additionally coated to enhance their transmission through the BBB. For example, one may employ hydrophilic-hydrophobic type polymeric surfactants, and preferably, a non-ionic surfactant such as a polyoxyethylene (20) sorbitan monooleate [polysorbate 80]. The hydrophilic groups in polysorbate 80 include polyether functionality and the hydrophobic groups include hydrocarbon functionality.

D. Nanoparticles in Hydrophilic and/or Hydrophobic Media

Nanoparticles of the API herein may be formed by physically reducing the size of the API, which may be achieved by a grinding, milling or pulverizing type operation. In such manner nanoparticles of the API may be prepared that provide the API such that, as noted above, it may have a largest linear dimension on the order of 1 nm to 999 nm, including all values and increments therein, such as between 1-900 nm, 1-800 nm, 1-700 nm, in 1 nm increments. Preferably, the range may be 10 nm to 300 nm. The API may include any of the aforementioned MMB4 dihalide and/or MMB4 DMS compounds. In addition, the API may be combined with a P-glycoprotein (PGB) inhibitor. Accordingly, the nanoparticles of the API may be placed in a liquid type hydrophobic and/or hydrophilic medium of the types noted herein.

In addition, prior to distribution in such mediums, the nanoparticles of the API may be coated with the above referenced hydrophilic-hydrophobic type polymeric surfactants which includes chemical functionality that is both capable of secondary interactions with water and those that do not indicate such interactions with water. For example, a non-ionic surfactant such as a polyoxyethylene (20) sorbitan monooleate [polysorbate 80]). In general, other suitable surfactants that are contemplated may include surfactants selected from fatty-acid esters of glycerols, sorbitol and other multifunctional alcohols, e.g., glycerol monostearate, sorbitan monolaurate, or sorbitan monooleate. In addition, one may utilize polysorbate 60, poloxamers, polyoxamines, polyoxyethylene ethers, polyoxyethylene esters, ethoxylated triglycerides, ethoxylated phenols and ethoxylated diphenols, metal salts of fatty acids, metal salts of fatty alcohol sulfates, sodium lauryl sulfate, metal salts of sulfosuccinates.

E. Calcium Phosphate Nanoparticles

The calcium phosphate nanoparticles that may be employed herein, for transport across the BBB, may include the calcium phosphate particles that are described in U.S. application Ser. No. 12/245,540 entitled "Modified Calcium Phosphate Nanoparticle Formation." These calcium phosphate nanoparticles are generally non-aggregating and may be prepared by mixing a solution of a calcium salt with a salt of phosphoric acid and adding an active ingredient to one of the calcium salt solution or phosphoric acid salt solution. This may then be followed by adjusting the pH to a level of greater than 7.0 and less than or equal to 10.0 and forming calcium phosphate nanoparticles and adding a polycation and/or polyanion and terminating the formation of said nanoparticles. The active ingredient may then be encapsulated in the nanoparticles, which nanoparticles may have a zeta potential of −50 to 50 millivolts (mV). The active ingredient may therefore include the MMB4 compounds noted herein.

The non-aggregating calcium phosphate nanoparticles may also be prepared by mixing a solution of a calcium salt with a salt of phosphoric acid and adding a polycation and/or polyanion. This may then be followed by adjusting the pH to a level of greater than 7.0 and less than or equal to 10.0 and forming calcium phosphate nanoparticles and adding a polycation and/or polyanion to terminate the nanoparticle formation. This may then be followed by adding an active ingredient to the nanoparticles (e.g. the MMB4 compounds noted herein) wherein the active ingredient is associated with the nanoparticle surface via a secondary bonding interaction (a bonding interaction other than a covalent bond). Therefore, in the case of the MMB4 compounds, it may be appreciated that the MMB4 with a net positive charge may preferably associate with the calcium phosphate particles that include a polyanion on the surface thereof.

The non-aggregating calcium phosphate particles herein may also include a combination of the above two protocols. For example, the calcium phosphate nanoparticles may include a polyanion on the surface thereof that is associated with one or more of the aforementioned MMB4 compounds, as well as having one or more of the MMB4 compounds encapsulated by the calcium phosphate particle.

Example 1

MMB4 DMS on Calcium Phosphate Nanoparticles

Calcium phosphate (CaP) nanoparticles associated with MMB4 DMS were prepared as disclosed in U.S. application Ser. No. 12/245,450. That is, a salt solution containing a polyanion is combined with a phosphate salt solution and the pH is adjusted to a level above 7.0 and less than or equal to 10 to provide for CaHPO$_4$ nanoparticle growth. Nanoparticle growth is then terminated by the addition of a sufficient amount of a polyanionic polymer, such as polyacrylic acid, polyglutamic acid and or anionic oligopeptide polymers. MMB4 DMS was added and left at ambient temperature for about four hours. The solids in the formed slurry were isolated and washed with deionized water before being lyophilized. The sample was analyzed to have 14% adsorbed MMB4 DMS.

Example 2

MMB4 DMS Encapsulated CaP Nanoparticles

MMB4 DMS was added to a starting solution of a calcium salt solution and a phosphate salt solution, followed by pH adjustment and CaHPO$_4$ nanoparticle growth. The growth may be terminated by addition of either a polycation or polyanion to provide a nanoparticle with encapsulated MMB4 DMS.

Example 3

Cellular Uptake of Polysorbate 80 Coated Nanoparticles

Calcium phosphate (CaP) nanoparticles with an encapsulated fluorescent indicator was prepared by addition of the fluorescent indicator to a solution of a calcium salt solution and a phosphate salt solution, followed by pH adjustment and CaHPO$_4$ nanoparticle growth. The growth may be terminated by addition of either a polycation or polyanion to provide a nanoparticle with encapsulated indicator. The particles were also coated with Polysorbate 80. Cellular uptake of these particles in Helsa cells was separately confirmed.

Example 4

MMB4 DMS Nanoparticles in Cottonseed Oil

MMB4 DMS nanoparticles were suspended in cottonseed oil and milled to stable nanoparticles. The particles were analyzed to be 20 nm to 200 nm in size (largest linear dimension) by both dynamic light scattering measurements and scanning electron microscopy (after drying and sputter coating). The mean size was 22.8 nm with a mean standard deviation of 8.1 nm.

Example 5

MMB4 DMS in Polysorbate 80

MMB4 DMS nanoparticles were suspended in polysorbate 80 and milled to stable nanoparticles. The particles were analyzed to have a mean size of 517 nm in size (largest linear dimension), with a mean standard deviation of 85 nm, by both dynamic light scattering measurement and scanning electron microscopy (after drying and sputter coating).

Example 6

MMB4 DMS Nanoparticles in Cottonseed Oil And Polysorbate 80 Mixture

MMB4 DMS nanoparticles in mixtures of cottonseed oil and polysorbate 80 with varying proportions were prepared. The compositions could be prepared either by a single milling process in the mixture or by a post-milling formulation.

Example 7

Preparation of MMB4 Dimethane Sulfonate (Laboratory Scale)

(1) Production of MMB4 Diiodide

To 21.53 g (0.176 mol) of pyridine-4-aldoxime in 250 mL of acetonitrile was added 27.21 g (0.176 mol) of diiodomethane. The reaction mixture was refluxed under argon for 90 hours. The mixture was cooled, filtered and the filter cake washed with 100 ml of acetonitrile. The filter cake was air dried for 30 minutes to yield 41.52 g. The cake was dried under high vacuum to give 41.02 g (91% yield).

(2) Dimethanesulfonate Resin Preparation In a 250 mL beaker, 30 g of Dowex 550A (OH form), available from the Dow Chemical Company, was added to 84 mL of 10% (v/v) methanesulfonic acid in methanol. The resin was stirred at room temperature for 2 h then filtered through a 150 mL sintered funnel. The resin bed was washed with 2×84 mL portions of methanol and then air-dried for 30 minutes. Total resin weight: 17.6 g, divided into 2×8.8 g portions.

(3) Conversion of MMB4 Diiodide to MMB4 Dimethanesulfonate

A sample of 2.0 g (3.9 mmol) of MMB4 diiodide was dissolved in 100 mL of methanol with stirring in a 50° C. water bath. The solution was cooled to room temperature, then 8.8 g of the mesylate form of Dowex 550A was added and stirred at room temperature for 2 hours. The mixture was filtered through a sintered funnel, washing the resin bed with 10 mL of methanol. An additional 8.8 g of the mesylate form of Dowex 550A was added to the filtrate and the mixture stirred for an additional 2 h. The mixture was filtered and the resin bed washed with 10 mL of methanol.

The filtrate was concentrated to 10 mL, then 35 mL of denatured ethanol (denatured with 5% isopropanol and 5% methanol) was added. The mixture was heated to 50° C. with stirring until complete dissolution (30 min). The solution was allowed to stand for 16 hours at ambient temperature with slow stifling. The mother liquor was decanted and the solids rinsed with 2×5 mL of cold (5° C.) denatured ethanol. The solid was dried at 23 mm Hg and room temperature to yield 1.35 g (77%) of a tan-amber solid (Polymorph A).

Example 8

Preparation of MMB4 Dimethanesulfonate (Production Scale)

(1) Production of MMB4 Diiodide

A 100-gallon (380 L) reactor is charged with 21.9 kg (179 moles) of pyridine-4-aldoxime and 170 kg of acetonitrile, followed by 48.3 kg (180 moles) of diiodomethane and 37.5 kg of acetonitrile. The mixture is brought to a gentle reflux (approximately 84° C.) with vigorous mechanical stifling under an inert atmosphere (nitrogen). After 72 hours, the mixture is cooled to 40-45° C. with stirring over 5 hours. The resulting suspension is filtered and then washed three times with 25 kg portions of 40-45° C. acetonitrile. The washed filter cake is transferred to drying trays and dried under vacuum with heating 40-45° C. over eight hours. This process yields approximately 37.5 kg (82%) of MMB4 diiodide.

(2) Dimethanesulfonate Resin Preparation

In a 100-gallon (380 L) reactor, 172 kg of methanol is slowly charged to methanesulfonic acid (35.7 kg), maintaining the temperature at 20-40° C. This solution is subsequently added to 77.5 kg of Dowex 550A (OH form), maintaining the temperature below 50° C. The resultant resin/methanol/methanesulfonic acid slurry is then stirred at 25±5° C. for 2-2.5 hours and then filtered. The resin is washed in a plug flow manner with two-153 kg portions of methanol. A final wash of 35 kg of methanol is used to test for residual water; the in-process limit is no more than 0.4%.

(3) Conversion of MMB4 Diiodide to MMB4 Dimethanesulfonate

In a 100-gallon (380 L) reactor, MMB4 diiodide, 10.3 kg, is dissolved in 204.5 kg of methanol with stifling by warming to 50±3° C. for 1-1.5 hours. While maintaining the temperature, half of the previously formed dimethanesulfonate resin is added and stirred at 50±3° C. for 2 to 2.5 hours. The solution is then filtered and the resin is washed with 20.5 kg of methanol. The filtrate and wash are combined and treated as described above with the remaining half of the resin.

After the final filtration and washing, an in-process test is used to monitor iodide concentration. The wash and filtrate are combined and then reduced to a volume of 65-70 L under vacuum at a temperature less than 25° C. After concentrating, 5.5 kg each of isopropanol and methanol are added followed by 98 kg of ethanol. The mixture is heated to reflux (approximately 72° C.) for 1-1.5 hour to achieve complete dissolution.

Once clarity is achieved, the mixture is allowed to cool to 20±5° C. over approximately 9 hours to crystallize, followed by an additional hold time of 7-7.5 hours. The MMB4 dimesylate is then filtered and washed with a mixture of 4.5 kg ethanol and 2.3 kg of methanol. The filter cake is then dried at ambient temperature under vacuum for 8 hours. The typical yield is 5-5.7 kg or 55-63% of MMB4 dimethanesulfonate (Polymorph B).

Example 9

A representative pharmaceutical formulation for MMB4 DMS is set forth below:

450 mg/mL of MMB4 DMS and 5 mg/mL of benzyl alcohol in WFI is adjusted with an acetic acid solution to a pH of about 2.3. The following were then transferred to a 5 mL volumetric flask: 25 mg benzyl alcohol (BA), 1.0 g "0.3% Acetic acid solution" and 2.25 g MMB4 DMS. At this point, WFI water is added to dissolve the solids completely. The pH is then measured and adjusted with acetic acid solution to a pH of about 2.3. At this point one brings the total volume to 5 mL with WFI water. This is then followed by filtering through a 0.2-micron syringe filter.

What is claimed is:

1. A nanoparticle for transport across the blood-brain barrier, comprising a polymeric resin, wherein said polymeric resin encapsulates a bis-quaternary pyridinium-2-aldoxime salt of the formula:

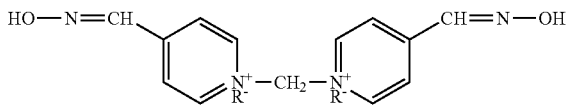

wherein said nanoparticle has a largest size dimension of 1 nm to 999 nm and R⁻ refers to an anionic counterion for the cationic charge associated with the nitrogen and R⁻ is a halogen and said polymeric resin comprises a polymer of the following structure:

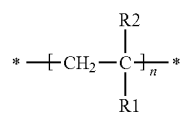

wherein R1 and/or R2 comprise a functional group that provides partial negative polarity to thereby facilitate attraction to said pyridinium salt;

and wherein said salt indicates one of the following:

(a) a plurality of distinguishing x-ray diffraction peaks at 2 Theta angles of 10-35 degrees as compared to non-distinguishing x-ray diffraction peaks at 2 Theta angles of greater than 35 degrees, wherein said distinguishing x-ray diffraction peaks have relative intensity counts between 500-1500 at 2 Theta angles of 10-35 degrees and non-distinguishing x-ray diffraction peaks have relative intensity counts of less than 500 at 2 Theta angles of greater than 35 degrees and no peaks are present with relative intensity accounts of more than 250 at 2 Theta angles between 35-60 degrees and wherein said salt has a particulate structure and an aspect ratio of 2:1 to 16:1; or (b) a plurality of distinguishing x-ray diffraction peaks at 2 Theta angles of 10-45 degrees as compared to non-distinguishing x-ray diffraction peaks at 2 Theta angles greater than 45 degrees, wherein said distinguishing x-ray diffraction peaks have relative intensity counts between 500-1500 at 2 Theta angles of 10-45 degrees and non-distinguishing x-ray diffraction peaks have relative intensity counts of less than 500 at 2 Theta angles of greater than 45 degrees and no peaks are present with relative intensity accounts of more than 250 at 2 Theta angles between 45-60 degrees and wherein said salt has a particulate structure comprising a square, rectangular, rhomboid or rhombus geometry.

2. The nanoparticle of claim 1 wherein R1 and/or R2 comprise a carbonyl group, a nitrile group, an amide group or a hydroxyl group.

3. The nanoparticle of claim 1 wherein said polymer comprises:

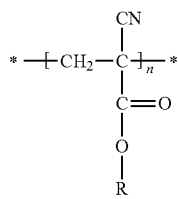

wherein R may be an alkyl group, an aromatic group or a substituted aromatic group.

4. The nanoparticle of claim 1 wherein said polymeric resin comprises one or more of the following: poly(lactic acid), poly(glycolic acid), poly(lactic acid)-poly(glycolic acid) copolymers, poly(lactic acid) or poly(glycolic acid) copolymers with poly(ethylene glycol), polyanhydrides, polyorthoesters, and polyphosphazines.

5. The nanoparticle of claim 1 wherein $R^-$ comprises a halide counterion selected from $Cl^-$, $Br^-$ or $I^-$.

6. A nanoparticle for transport across the blood-brain barrier, comprising a polymeric resin, wherein said polymeric resin encapsulates a bis-quaternary pyridinium-2-aldoxime salt of the formula:

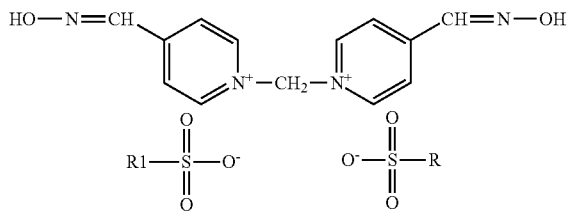

wherein R comprises an alkyl group and said nanoparticle has a largest size dimension of 1 nm to 999 nm;
said polymeric resin comprises a polymer of the following structure:

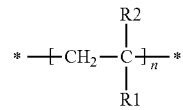

wherein R1 and/or R2 comprise a functional group that provides partial negative polarity to thereby facilitate attraction to said pyridinium salt;

and wherein said salt indicates one of the following:

(a) a plurality of distinguishing x-ray diffraction peaks at 2 Theta angles of 10-30 degrees as compared to non-distinguishing peaks at 2 Theta angles greater than 30 degrees and said salt has cubic rectangular crystal geometry, wherein said distinguishing x-ray diffraction peaks have relative intensity counts between 500-1500 at 2 Theta angles of 10-30 degrees and non-distinguishing x-ray diffraction peaks have relative intensity counts of less than 500 at 2 Theta angles of greater than 30 degrees and no peaks are present with relative intensity accounts of more than 250 at 2 Theta angles between 30-60 degrees and wherein said salt has a particulate structure comprising cubic rectangular geometry; or (b) a plurality of distinguishing x-ray diffraction peaks at 2 Theta angles of 10-30 degrees as compared to non-distinguishing peaks at 2 Theta angles greater than 30 degrees and said salt has hexagonal crystal structure, wherein said distinguishing x-ray diffraction peaks have relative intensity counts between 1000-4500 at 2 Theta angles of 10-30 degrees and non-distinguishing x-ray diffraction peaks have relative intensity counts of less than 500 at 2 Theta angles of greater than 30 degrees and no peaks are present with relative intensity accounts of more than 500 at 2 Theta angles between 35-60 degrees and wherein said salt has a particulate structure comprising hexagonal structure.

7. The nanoparticle of claim 1 wherein said nanoparticles have a surface which includes apolipoprotein on said surface of said particles.

8. The nanoparticle of claim 1 wherein said nanoparticles have a surface which includes folic acid on said surface of said particles.

9. The nanoparticle of claim 1 wherein said nanoparticles have a surface which includes non-specific targeting on said surface comprising Tat based targeting.

10. The nanoparticle of claim 6 wherein said nanoparticles have a surface which includes apolipoprotein on said surface of said particles.

11. The nanoparticle of claim 6 wherein said nanoparticles have a surface which includes folic acid on said surface of said particles.

12. The nanoparticle of claim 6 wherein said nanoparticles have a surface which includes non-specific targeting on said surface comprising Tat based targeting.

* * * * *